(12) United States Patent
Öhman et al.

(10) Patent No.: US 8,877,142 B2
(45) Date of Patent: Nov. 4, 2014

(54) ASSAY DEVICE AND METHOD

(75) Inventors: Per Ove Öhman, Uppsala (SE); Ib Mendel-Hartvig, Uppsala (SE)

(73) Assignee: Johnson & Johnson AB (SE)

( * ) Notice: Subject to any disclaimer, the term of this patent is extended or adjusted under 35 U.S.C. 154(b) by 529 days.

(21) Appl. No.: 12/305,630

(22) PCT Filed: Jun. 20, 2007

(86) PCT No.: PCT/SE2007/050444
§ 371 (c)(1),
(2), (4) Date: Apr. 14, 2009

(87) PCT Pub. No.: WO2007/149042
PCT Pub. Date: Dec. 27, 2007

(65) Prior Publication Data
US 2009/0208920 A1    Aug. 20, 2009

(30) Foreign Application Priority Data

Jun. 20, 2006 (SE) ....................... 0601354

(51) Int. Cl.
| | |
|---|---|
| *B01L 3/00* | (2006.01) |
| *G01N 33/52* | (2006.01) |
| *G01N 33/558* | (2006.01) |
| *G01N 35/00* | (2006.01) |

(52) U.S. Cl.
CPC ......... *B01L 3/502746* (2013.01); *B01L 3/5023* (2013.01); *B01L 2300/0896* (2013.01); *B01L*
(Continued)

(58) Field of Classification Search
CPC ............. B01L 3/5027; B01L 3/50273; B01L 2300/0896; B01L 2300/0848–2300/0858; B01L 2300/0809; B01L 2300/0816; B01L 2400/086; B01L 2400/0406; G01N 2035/00237

USPC ................ 435/287.1; 436/514; 422/500–508, 422/555–559
See application file for complete search history.

(56) References Cited

U.S. PATENT DOCUMENTS

| | | | |
|---|---|---|---|
| 5,096,836 A | * | 3/1992 | Macho et al. ................. 436/169 |
| 6,143,576 A | | 11/2000 | Buechler |

(Continued)

FOREIGN PATENT DOCUMENTS

| | | |
|---|---|---|
| EP | 0 297 389 | 1/1989 |
| JP | 2000-055911 | 2/2000 |

(Continued)

OTHER PUBLICATIONS

Lonza Rockland, Inc., GelBond Film, 2007, pp. 1-3.*

(Continued)

*Primary Examiner* — Melanie Y Brown
*Assistant Examiner* — Erik B Crawford
(74) *Attorney, Agent, or Firm* — Hiscock & Barclay, LLP (57) ABSTRACT

There is provided an assay device comprising a lid and a base, said base comprising, a sample addition zone, a reaction zone and an absorbing zone, said components being in fluid connection and being part of a fluid passage leading from the sample addition zone to the absorbing zone, wherein: (a) a sample addition well is integrated in the lid, (b) the absorbing zone consists of an area on an non-porous substrate, having substantially perpendicular projections, said projections defining a volume, which together with the volume of the fluid passage defines the sample volume subjected to the assay, and (c) at least one filter is between the sample addition well and the sample addition zone. There is further provided methods for handling samples.

7 Claims, 3 Drawing Sheets

(52) U.S. Cl.
CPC ......... 2300/0825 (2013.01); *G01N 2035/00237*
(2013.01); *B01L 3/5027* (2013.01); *B01L*
*2400/086* (2013.01); *B01L 2300/0816*
(2013.01); *B01L 2300/0809* (2013.01); *G01N*
*33/525* (2013.01); *B01L 2300/0681* (2013.01);
*G01N 33/558* (2013.01); *B01L 2400/0406*
(2013.01); *B01L 3/50273* (2013.01); *B01L*
*2400/088* (2013.01)
USPC ....... 422/412; 422/68.1; 422/82.05; 422/402;
422/507; 422/947; 436/174; 435/283.1;
435/287.1; 435/287.7

(56) References Cited

U.S. PATENT DOCUMENTS

| | | | |
|---|---|---|---|
| 6,156,270 | A | 12/2000 | Buechler |
| 6,261,519 | B1 | 7/2001 | Harding et al. |
| 6,312,888 | B1 | 11/2001 | Wong et al. |
| 6,767,510 | B1 | 7/2004 | Buechler |
| 6,767,710 | B2 * | 7/2004 | DiNello et al. ............... 435/7.1 |
| 6,846,453 | B1 | 1/2005 | Uesaka et al. |
| 7,045,342 | B2 | 5/2006 | Nazareth et al. |
| 2003/0035758 | A1 | 2/2003 | Buechler et al. |
| 2004/0077103 | A1 | 4/2004 | Buechler |
| 2004/0126767 | A1 | 7/2004 | Anderberg et al. |
| 2005/0092666 | A1 * | 5/2005 | Wilson ......................... 210/136 |
| 2005/0136552 | A1 | 6/2005 | Buechler |
| 2007/0269893 | A1 * | 11/2007 | Blankenstein et al. .......... 436/2 |

FOREIGN PATENT DOCUMENTS

| | | |
|---|---|---|
| JP | 2003-512624 | 4/2003 |
| JP | 2004-008132 | 1/2004 |
| JP | 2004-045357 | 2/2004 |
| JP | 2004-093558 | 3/2004 |
| JP | 2005-230816 | 9/2005 |
| WO | WO 01/29558 A1 | 4/2001 |
| WO | WO 03103835 A1 * | 12/2003 |
| WO | WO-2005/089082 A2 | 9/2005 |
| WO | WO 2005/089082 A3 | 9/2005 |
| WO | WO 2005119211 A1 * | 12/2005 |

OTHER PUBLICATIONS

Lonza Rockland, Inc., GelBond Film, retrieved on May 30, 2012, pp. 1-3.*

International Preliminary Report on Patentability completed Sep. 5, 2008 for PCT Application No. PCT/SE2007/050444 filed Jun. 20, 2007, 5 pages.

International Search Report mailed Oct. 22, 2007 for PCT Application No. PCT/SE2007/050444 filed Jun. 20, 2007, 4 pages.

International Written Opinion mailed Jun. 16, 2008 for PCT Application No. PCT/SE2007/050444 filed Jun. 20, 2007, 5 pages.

International Written Opinion mailed Oct. 22, 2007 for PCT Application No. PCT/SE2007/050444 filed Jun. 20, 2007, 5 pages.

European Office Action for EP Application No. 07 748 604.1; dated Mar. 22, 2011; 3 pages.

Japanese Office Action for JP Application No. 2009-516452; dated Jan. 10, 2012; 3 pages.

* cited by examiner

ASSAY DEVICE AND METHOD

CROSS REFERENCE TO RELATED APPLICATIONS

This is a U.S. National Phase patent application of PCT/SE2007/050444, filed Jun. 20, 2007, which claims priority to Swedish patent application Serial No. 0601354-4 filed Jun. 20, 2006, all of which are hereby incorporated by reference in the present disclosure in their entirety.

The present invention concerns an assay device with integrated functions which improves the device.

BACKGROUND

Many biochemical tests formerly performed in the laboratory using advanced equipment and skilled technicians can today be performed by a physician, a nurse or even the patient himself/herself, using small, often disposable devices. This is one result of a better understanding of biochemistry and medicine, as well as the ongoing miniaturization of both mechanics and electronics, taking place over the recent decades.

Such tests can be divided into two groups: "one-step tests" where a reaction takes place on a substrate after the addition of sample, and the result is detected as a change of one or more properties of said substrate; and "two-step tests", where the sample is followed by the addition of a detection conjugate, leading to a specific reaction resulting in a detectable signal.

In most assays, the detection conjugate and possible other reagents are pre-dispensed or integrated in the device, setting aside the need for separate addition of reagents by the user.

The most common type of disposable assay device consists of a zone or area for receiving the sample, a reaction zone, and optionally a transport or incubation zone connecting the receiving and reaction zone, respectively. These assay devices are known as immunochromatography assay devices or simply referred to as strip tests. They employ a porous material, such as nitrocellulose, defining a fluid passage capable of supporting capillary flow. The sample-receiving zone frequently consists of a more porous material, capable of absorbing the sample, and, when the separation of blood cells is desired, effective to trap the red blood cells. Examples of such materials are fibrous materials, such as paper, fleece, gel or tissue, comprised e.g. of cellulose, nitrocellulose, wool, glass fibre, asbestos, synthetic fibres, polymers, etc. or mixtures of the same. The transport or incubation zone commonly consists of the same or similar materials, often with different porosity than that of the sample-receiving zone. Likewise, the reaction zone, which may be integrated with the incubation zone, or constituting the most distal part thereof, commonly consists of similar, absorbing fibrous materials, such as nitrocellulose, or any of the above listed materials.

Nitrocellulose materials are also frequently used as the matrix constituting the transport or reaction zone, or connecting the receiving zone and the reaction zone. A significant disadvantage with nitrocellulose is its high non-specific binding of proteins and other bio-molecules. Present test strips however often handle a surplus of sample, reducing the influence of this binding. Another disadvantage of nitrocellulose is its variations with regard to both chemical and physical quality. It is in any case desirable to minimize the sample volume, in line with the tendency to miniaturize the entire test, including minimizing the amounts of reagents, without compromising accuracy and reliability.

In an assay device or strip test, the porous material/-s is/are assembled on a carrier, such as a strip of thermoplastic material, paper, cardboard or the like. Further, a cover can be provided, said cover having at least one aperture for receiving the sample, and an aperture or a transparent area for reading the result of the assay.

Frequently this cover is simultaneously a housing or case, enclosing the porous material, providing stability and structural protection. Examples of such constructions include published U.S. patent application Ser. No. 10/794,516, published as 2004171174, international publication number WO2004/038414, or U.S. Pat. No. 6,846,453.

U.S. Pat. No. 6,312,888 discloses an assay device comprising several layers for the analysis of an analyte in a biological sample.

From WO2005/089082 there is known a device for handling liquid samples, comprising an area having projections substantially vertical to its surface, whereby the projections create a capillary force. In such assay devices there arise new problems compared to earlier assay devices without projections creating a capillary force.

Problems in the state of the art regarding assay devices include how to improve the sample addition, how to improve the hematocrit tolerance for blood samples, and how to protect the assay device from damage from a pipette, when a pipette is used to add a liquid to said assay device.

SUMMARY OF THE INVENTION

It is an object of the present invention to address the disadvantages associated with known assay devices, and to provide an improved assay device, alleviating at least some of the problems in the prior art. Further disadvantages associated with known devices and the advantages associated with the embodiments of the invention will be apparent to skilled person upon a closer study of the description, examples and claims.

The present invention makes available an assay device as defined in the claims, incorporated herein by reference.

Further aspects of the invention, as well as their advantages, will become evident to the skilled person upon closer study of the description, examples, claims and drawings.

DESCRIPTION OF THE DRAWINGS

The invention will be described in detail in the following description, non-limiting examples, and claims, with reference to the attached drawings, in which

DESCRIPTION

Assays can be classified into two groups, based on the criteria that have the greatest influence on the performance that can be expected of an assay with regard to precision and sensitivity:

competitive assays, i.e. assays using a limited amount of antibody, and solid phase sandwich assays, using an excess amount of antibody, also called immunometric assays.

In the competitive assay format, the amount of antibody is insufficient to bind all of the antigens. A fixed amount of labelled antigen competes with the unlabelled antigen from the sample for the limited amount of antibody binding sites. The concentration of antigen in the sample can be determined from the proportion of labelled antigen that is bound to the antibody or alternatively that is free.

In the sandwich assay format, the antigen present in the sample binds to excess of antibodies on the solid phase. The bound antigen is then detected with a second labelled antibody. In this instance, the amount of labelled antibody captured on the solid phase is directly proportional to the amount of antigen in the sample.

In both these basic designs of immunoassays, and the various variants thereof, there is a big need for standardization and control of the assay and the environment the assay is run in. The embodiments of the present invention address some of the problems connected with solid phase lateral flow immunoassay. One of the crucial steps is the solubilisation and transport of the detection conjugate. Another important step is the separation of red blood cells where there is a high risk for cell lysis and blood clotting.

The invention is not restricted to the assay format described above but can of course also be adapted to other assay format well known for persons skilled in the art.

Before the present device and method is described, it is to be understood that this invention is not limited to the particular configurations, method steps, and materials disclosed herein as such configurations, steps and materials may vary somewhat. It is also to be understood that the terminology employed herein is used for the purpose of describing particular embodiments only and is not intended to be limiting since the scope of the present invention will be limited only by the appended claims and equivalents thereof. It must also be noted that, as used in this specification and the appended claims, the singular forms "a", "an", and "the" include plural referents unless the context clearly dictates otherwise. Thus, for example, reference to a reaction mixture containing "a monoclonal antibody" includes a mixture of two or more antibodies.

The term "about" when used in the context of numeric values denotes an interval of accuracy, familiar and acceptable to a person skilled in the art. Said interval can be ±10% or preferably ±5%.

In describing and claiming the present invention, the following terminology will be used in accordance with the definitions set out herein.

The term "sample" here means a volume of a liquid, solution or suspension, intended to be subjected to qualitative or quantitative determination of any of its properties, such as the presence or absence of a component, the concentration of a component, etc. The sample may be a sample taken from an organism, such as a mammal, preferably a human; or from the biosphere, such as a water sample, or an effluent; or from an technical, chemical or biological process, such as a process of manufacturing, e.g. the production of medicaments, food, feed, or the purification of drinking water or the treatment of waste effluents. The sample may be subjected to qualitative or quantitative determination as such, or after suitable pretreatment, such as homogenization, sonication, filtering, sedimentation, centrifugation, heat-treatment etc.

Typical samples in the context of the present invention are body fluids such as blood, plasma, serum, lymph, urine, saliva, semen, amniotic fluid, gastric fluid, phlegm, sputum, mucus, tears etc.; environmental fluids such as surface water, ground water, sludge etc.; and process fluids such as milk, whey, broth, nutrient solutions, cell culture medium, etc. The embodiments of the present invention are applicable to all samples, but preferably to samples of body fluids, and most preferably to whole blood samples.

The determination based on lateral flow of a sample and the interaction of components present in the sample with reagents present in the device and detection of such interaction, either qualitatively or quantitatively, may be for any purpose, such as diagnostic, environmental, quality control, regulatory, forensic or research purposes. Such tests are often referred to as chromatography assays, or lateral flow assays, as in e.g. immunochromatography assays.

Examples of diagnostic determinations include, but are not limited to, the determination of analytes, also called markers, specific for different disorders, e.g. chronic metabolic disorders, such as blood glucose, blood ketones, urine glucose (diabetes), blood cholesterol (atherosclerosis, obesitas, etc); markers of other specific diseases, e.g. acute diseases, such as coronary infarct markers (e.g. troponin-T), markers of thyroid function (e.g. determination of thyroid stimulating hormone (TSH)), markers of viral infections (the use of lateral flow immunoassays for the detection of specific viral antibodies); etc.

Another important field of diagnostic determinations relate to pregnancy and fertility, e.g. pregnancy tests (determination of i.a. human chorionic gonadotropin (hCG)), ovulation tests (determination of i.a. luteneizing hormone (LH)), fertility tests (determination of i.a. follicle-stimulating hormone (FSH)) etc.

Yet another important field is that of drug tests, for easy and rapid detection of drugs and drug metabolites indicating drug abuse; such as the determination of specific drugs and drug metabolites (e.g. THC) in urine samples etc.

The term "analyte" is used as a synonym of the term "marker" and intended to encompass any substance that is measured quantitatively or qualitatively.

The terms "zone", "area" and "site" are used in the context of this description, examples and claims to define parts of the fluid passage on a substrate, either in prior art devices or in a device according to an embodiment of the invention.

The term "reaction" is used to define any reaction, which takes place between components of a sample and at least one reagent or reagents on or in said substrate, or between two or more components present in said sample. The term "reaction" is in particular used to define the reaction, taking place between an analyte and a reagent as part of the qualitative or quantitative determination of said analyte.

The term "base" here means the carrier or matrix to which a sample is added, and on or in which the determination is performed, or where the reaction between analyte and reagent takes place.

The term "chemical functionality" comprises any chemical compound or moiety necessary for conducting or facilitating the assay. One group of chemical compounds, with particular relevance in the present invention, are compounds or components exhibiting specific affinity to, or capability of binding or interacting with, one or more components in the sample. Red blood cell separating agents constitute an illustrative example. Such agents may be any substance capable of aggregating or binding red blood cells.

The term "biological functionality" comprises all biological interactions between a component in a sample and a reagent on or in the substrate, such as catalysis, binding, internalization, activation, or other bio-specific interaction. Suitable reagents include, but are not limited to, antibodies, antibody fragments and derivates, single chain antibodies, lectines, DNA, aptamers, etc., including other polymers or molecules with binding capacity. Such reagents can be identified by a person skilled in the art, following the choice of the component to be separated, using standard experimentation, e.g. screening methods and chemical libraries.

The term "physical functionality" here comprises functionalities involved in reactions and interactions other than those that are mainly chemical or biological. Examples include diameter, height, shape, cross section, surface topography and surface patterns, the number of projections per unit area, wetting behaviour of the surface of said projections, or a combination thereof, and/or other functionalities influencing the flow, retention, adhesion or rejection of components of the sample.

The distinctions between chemical, biological and physical interactions are not always clear, and it is possible that an interaction—such as an interaction between a component in a sample and a reagent on the substrate—involves chemical, biological as well as physical zones.

The terms "hydrophilic" and "hydrophobic", as in hydrophilic or hydrophobic compounds, hydrophilic or hydrophobic interactions etc. have the meaning generally understood by a person skilled in the art, and corresponding to that used in generally recognized textbooks.

The present invention provides an assay device comprising a lid and a base, said base comprising a sample addition zone, a reaction zone and an absorbing zone, said components being in fluid connection and being part of a fluid passage leading from the sample addition zone to the absorbing zone, wherein (a) a sample addition well is integrated in the lid (b) the absorbing zone consists of an area on an non-porous substrate, having substantially perpendicular projections, said projections defining a volume which together with the volume of the fluid passage defines the sample volume subjected to the assay, and (c) at least one filter is between the sample addition well and the sample addition zone.

Embodiments of the present invention are directed to devices including at least one fluid passage for fluid transport, having a first end and a second end; and an absorbing zone specifically adapted to establish, maintain and/or meter fluid transport through or along said at least one fluid passage, wherein said absorbing zone comprises a non-porous substrate having a substrate surface, said zone having projections substantially perpendicular to said surface, and said projections having a height (H), diameter (D) and a distance or distances between the projections (t1, t2) such, that lateral capillary flow of said fluid in said zone is achieved.

Other embodiments concern methods for handling fluid transport in or along at least one fluid passage on or in a substrate, wherein the fluid transport in said passage is established and/or maintained and/or metered by an absorbing zone, arranged in fluid contact with said passage, and said absorbing zone comprising an zone made of a non-porous substrate, said zone having projections substantially perpendicular to said surface, and said projections having a height (H), diameter (D) and a distance or distances between the projections (t1, t2) such, that lateral capillary flow of said fluid on said zone is achieved.

In a device according to the invention, the capacity of the device is accurately determined by the volume defined by the absorbing zone. When sample is added in excess, the volume subjected to the assay will always be identical, due to the well-defined and reproducible non-porous structure. The flow rate can in turn be influenced and controlled by proper selection of the dimensions of the substantially vertical projections, their diameter, height and distances between the projections, as well as by adjusting their chemical, biological or physical properties, e.g. by coating the projections with a suitable compound. According to one embodiment, the projections are made hydrophilic by the addition of dextran. The flow rate can also be further adjusted by selecting a suitable degree of hydrophilicity of the foil, or that of an adhesive used to attach the foil to the projections.

The present assay device comprises a sample addition well. The sample addition well is integrated in the lid. The present assay device further comprises at least one filter. The sample addition well and the filter together give better separation of the sample. An advantage of the sample addition well integrated in the lid is that no leakage can occur at the sample addition well. A sample addition well gives protection against tiny drops of liquid sample which may splash during sample addition.

The additional filter makes the device insensitive or less sensitive to variations in hematocrit.

The assay device includes a filter for separating components in the sample. This filter is preferably a hydrophilic polymeric membrane capable of separating red blood cells from plasma, preferably without haemolysis, without non-specific protein binding, with high separation efficiency, and without red blood cell leakage. The Primecare® separation membranes (Spectral® Diagnostics Inc., Toronto, ON, Canada) are examples of such filters.

A foil can be arranged on the projections, thus accurately defining a volume between the projections, limited on one side by the substrate surface and on the other side, by said foil. It has been surprisingly shown that the addition of a foil influences the capillarity of the absorbing zone, and by choosing a suitable foil material and adhesives for fastening the foil, the hydrophilic properties of the absorbing zone can be adjusted as desired.

The device according to the invention is practically closed, and requires minimal interaction by the user. Once sample has been added, it remains only to insert the device into an apparatus for reading the result. Leakage of sample from the device is unlikely, which minimizes the risks for contamination of the reader. The device is easy to manufacture and, in its preferred embodiments, consists of only a few parts or only two main components, the support and the lid. The lid serves to protect the features of the support from the environment, dust, mechanical damage etc.

Further, the construction and the principle of reading the results from below, through the non-porous substrate, also aids in the creation of a closed system and protects the reader from contamination as the surfaces with sample, e.g. a patient sample, are not accessible to the reader or to the user. The lid also provides an area for labels and barcodes. Further advantages of the device include that it does not require disassembly for determination of the assay result.

It is however conceived that the device can have an element opposite to the lid. The bottom can be viewed as an element on the opposite side to the fluid passage. A bottom is protecting the other side of the base from mechanical damage, contamination or the like, that could influence the determination of the assay result. A bottom preferably has an aperture or other means enabling the reading of the assay result. According to one embodiment, not shown, the device has sliding means protecting the base of the device, but possible to remove or displace before the assay result is determined. In one embodiment the bottom has at least one opening so that the base can be read.

In one embodiment the air space above the base is in contact with the surrounding air only to a very small extent, through for instance at least one small opening. These has the advantage that air inside will be saturated or close to saturated with solvent vapours from the sample and thus prevent or delay further drying of the sample. Thus this particular embodiment leads to a slower drying of the sample on the base. One example of such an embodiment is an embodiment with a light tight lid or a bottom and a lid.

Importantly, the sample volume is not critical for the performance of the assay, as it is the total available volume of the absorbing zone and the fluid passage that determines the amount of sample. The assay becomes highly reliable as the absorbing zone, and in a preferred embodiment, also the fluid passage, consists of a well defined structure, possible to manufacture in a identical configuration from test to test, with no or negligible variations in volume, capacity or performance.

Figure 1:
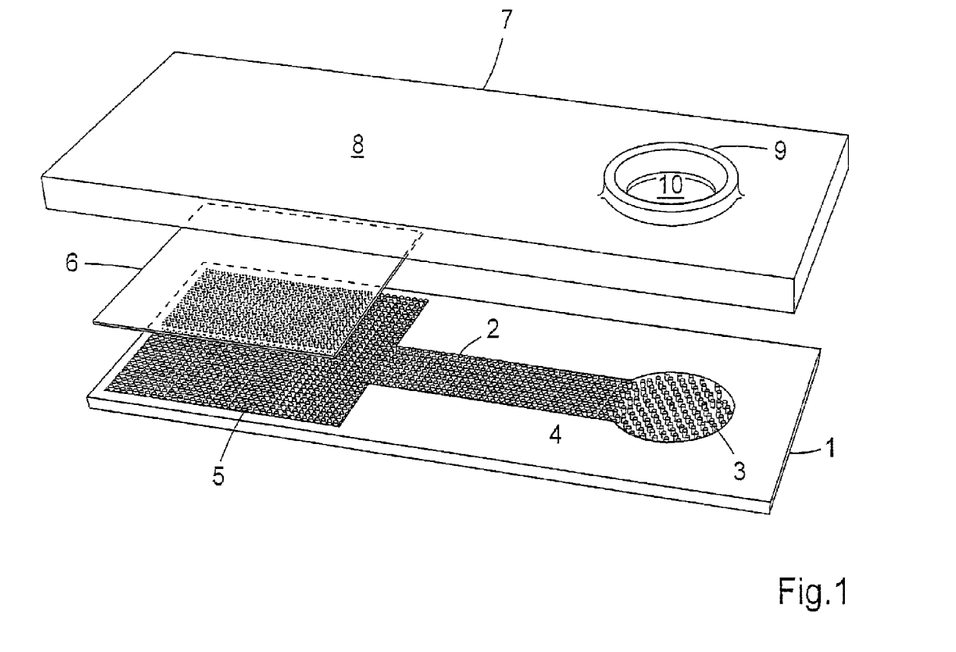
FIG. 1 shows an exploded view of an embodiment of the invention.

FIG. 1 shows an exploded view of an embodiment of the invention, where on the surface of a substrate or base 1 a flow path or fluid passage 2 is formed by projections, substantially perpendicular to said surface. These projections have a diameter, height and distance between them such, that lateral capillary flow is achieved. The projections are preferably modified with respect to their chemical, biological or physical functionality, and given hydrophilic properties, e.g. by the addition of dextran.

On the substrate surface, i.e. the base surface, a sample addition zone 3 is formed. Said zone can contain substantially vertical projections, but can also be a depression or well in the substrate. It is conceived that the sample addition zone at least partially contains said substantially perpendicular projections. FIG. 1 schematically shows an embodiment where the sample addition contains substantially vertical projections, but where said substantially vertical projections other properties, e.g. different dimensions, than those constituting the fluid passage 2.

Close to the sample addition zone, in the direction of flow, a detection conjugate is pre-dispensed in an area 4. Alternatively, the detection conjugate is pre-dispensed in the sample addition zone. At the end of the fluid passage 2 is an absorption zone 5, consisting of substantially perpendicular projections.

According to a preferred embodiment, the absorbing zone is covered by a foil 6, together with the surface of the substrate and the projections defining a volume.

In one embodiment there is a device in the sample addition well preventing a pipette from being inserted through the filter. In one embodiment this narrow opening is adapted to the pipette that is intended to be used together with the device so that the opening does not allow the pipette to be inserted completely through the opening. In an alternative embodiment the device is shaped so that the geometry of the opening and the pipette interacts and prevents the pipette to be inserted so that it damages the filter.

FIG. 1 further shows how a lid 7 can be arranged on the base 1. The lid 7 has at least one surface 8 for carrying information, such as printed information, text, pictures, bar codes etc. On the lid is also arranged a sample addition well 9, having a sample pretreatment filter 10.

Figure 2:
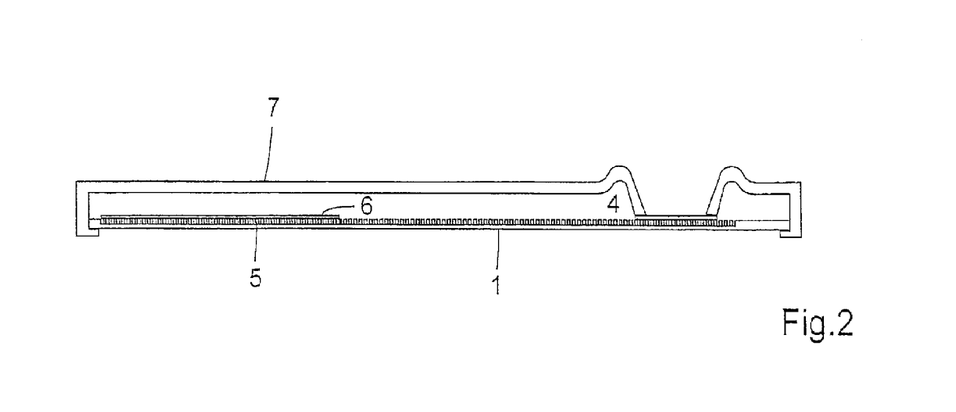
FIG. 2 shows a side view of an embodiment of the invention.

The side view shown in FIG. 2 illustrates how the sample pretreatment filter is in contact with the projections present on the sample addition zone 3. The side view also indicates that the lid 7 can be attached to the base 1 in a snap-lock fashion. It can also be glued, welded or otherwise attached to the base. A skilled person will chose a suitable method for attaching the lid to the base.

It is also conceived that the lid extends at least partially over the bottom surface of the base, protecting the base from scratches, dirt or other contamination or other influence that may compromise the reading of the assay result.

Figure 3:
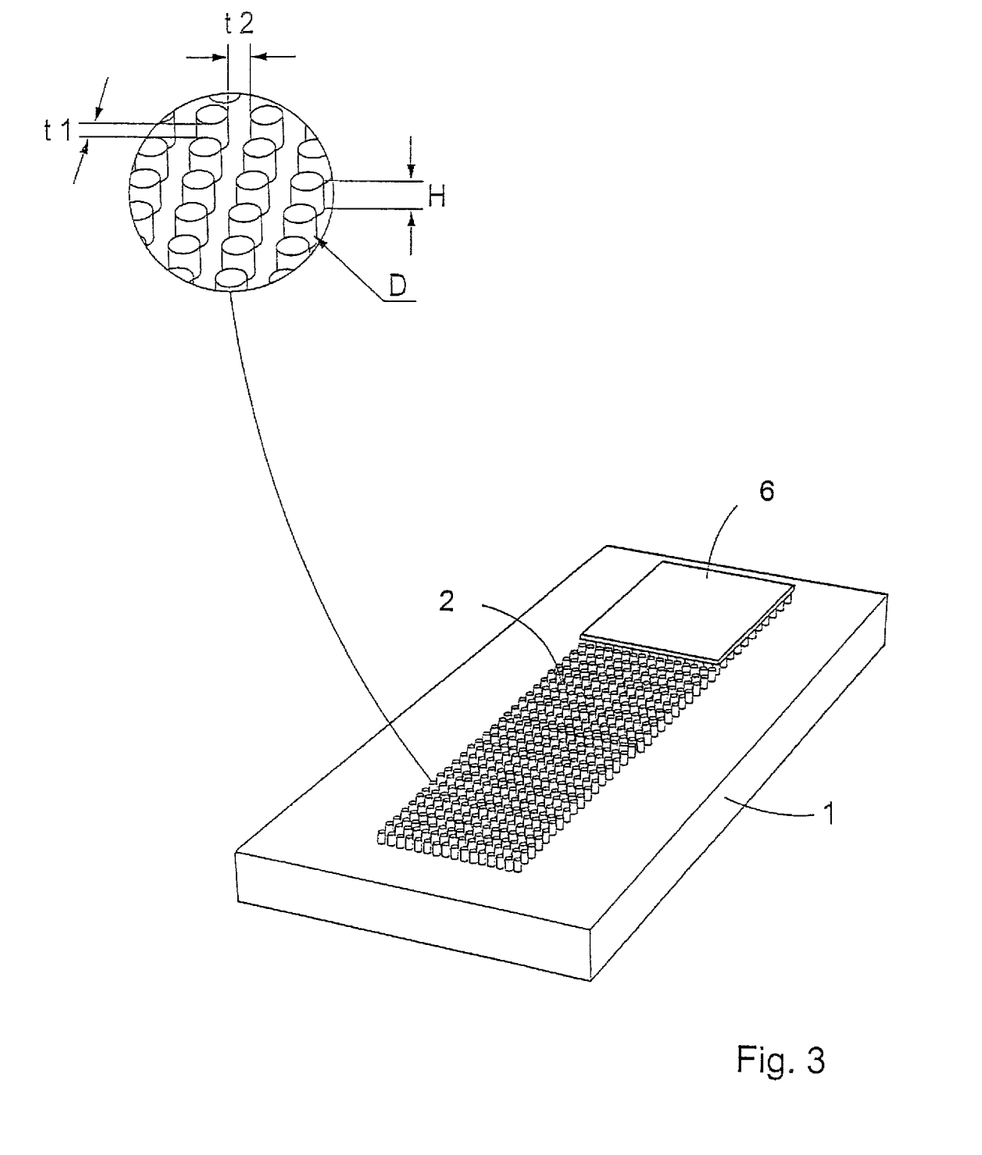
FIG. 3 shows schematically an embodiment having a fluid passage, and a detail of said fluid passage, illustrating the dimensions of the substantially perpendicular projections.

FIG. 3 shows schematically how a flow passage 2 is arranged on a base 1, said flow passage consisting of projections substantially perpendicular to the surface of the base, and an absorbing zone, covered by a foil 6. The detail shows how the dimensions of the projections, diameter, height and distance between the projections, are measured.

Figure 4:
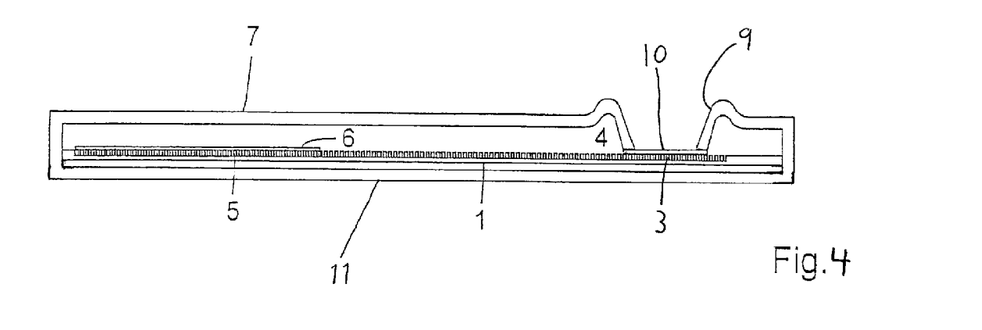
FIG. 4 shows an embodiment having a lid, a filter, a base and a bottom.

FIG. 4 shows an alternative embodiment of the present invention with a bottom 11. In addition to the bottom there is shown a base 1, comprising projections substantially perpendicular to said surface. The projections have a diameter, height and distance between then such that at least one capillary flow is achieved. In this particular embodiment there is one absorbing zone 5 covered by a foil 6, which together with the surface of the base and the projections define a volume. There is a cover or lid 7 protecting the device. In the lid there is integrated a sample addition well 9. Between the sample addition well 9 and the sample addition zone 3 there is arranged a sample pretreatment filter 10. The device further comprises a bottom 11 with an opening. The opening allows reading of the base 1 by a reader.

EXAMPLES

Materials and Methods

Micropillar structures as described in WO 03/103835 were produced by Åmic AB, Uppsala, Sweden, and used to form the sample addition zone, the reaction zone and the absorbing zone. Multiple test structures were manufactured on a thermoplastic disc, 1 mm thick, which was cut into strips, each having a fluid passage or open flow channel consisting of perpendicular projections or micropillars. The material used for manufacturing the disc was Zeonor® (Zeon Corp., Japan) a cyclic olefin polymer having excellent optical properties.

A positive master including the structures to be tested was made by etching the structures in silica, and a negative mold as made in nickel, using said silica master. Multiple test structures were manufactured by thermoplastic extrusion against the negative mold, producing the structures on a polypropylene disc, 1 mm thick, which was cut into strips, each having a fluid passage or open flow channel consisting of perpendicular projections or micropillars.

The micropillars had the following dimensions: 69 μm in height, 46 μm in diameter and placed at approximately 29 μm distance or distances from each other. The flow channel had a length of 25 mm and a width of 5 mm. The last 5 mm was used as support for the absorbing materials, defining an absorbing zone of about 5×5 mm.

The strips were given the same dimensions as a typical microscope slide, i.e. 20×76 mm, for practical reasons.

The steady state flow was measured by applying 10 μL of a buffer, composed of 0.25% Triton X-100, 0.5% BSA, 0.3M NaCl, 0.1 M Tris-buffer pH 7.0, in sequence five times. The time for the disappearance of buffer was timed. The last five was used for steady state calculation.

Example 1

Capillary Flow Using Porous Micro Beads as Absorbing Means 25 mg of dry Sephadex G25 (medium, Amersham Biosciences, Uppsala, Sweden) was placed at the far end of the flow channel, dispersed among the perpendicular projections. The flow was measured by buffer additions as described above. The results are shown in Table 1:

TABLE 1

| Addition | Chip A μL/min | Chip B μL/min |
|---|---|---|
| 1 | 7.1 | 7.1 |
| 2 | 6.7 | 7.0 |
| 3 | 6.7 | 6.8 |
| 4 | 6.9 | 6.7 |
| 5 | 7.1 | 7.1 |

Preliminary experiments using another fraction of the same micro beads, Sephadex G25 (superfine, Amersham Biosciences, Uppsala, Sweden) indicated that the particle size significantly influences the flow.

Example 2

Capillary Flow Using Cellulose/Glass Fiber Filters as Absorbing Means

A 25 mm long and 5 mm wide CF6 (Whatman, Maidstone, England) absorbing filter was placed at the far end of the flow channel, resting on the perpendicular projections. The flow was measured by buffer additions as described above. The results are shown in Table 2:

TABLE 2

| Addition | Chip C μL/min | Chip D μL/min |
|---|---|---|
| 1 | 11 | 11 |
| 2 | 12 | 11 |
| 3 | 12 | 10 |
| 4 | 11 | 11 |
| 5 | 11 | 11 |

The results indicate that a well functioning interface was formed between the fluid passage, the projections and the absorbing filter material, and that significant flow rated were achieved.

Example 3

Capillary Flow Using Foam Material as Absorbing Means

Polyurethane foam was cured in situ on the device, in the far end of the flow channel, in an area consisting of perpendicular projections. The foam filled the space between the projections, providing good fluid communication with the remaining flow channel. The time for 100 ul to be absorbed by the foam was measured three times for different samples. The results (Table 3) showed that a foam can serve as the absorbing zone and that relevant flow is achieved. It is anticipated that optimization of the foam with regard to porosity, curing and other properties, will result in even better flow rates.

TABLE 3

Obtained results for wicking. The y axis reports time to absorb 100 L of water

| Sample | time 1 | time 2 | time 3 | Average |
|---|---|---|---|---|
| 1.1 | 2.30 | 4.30 | 3.10 | 3.23 |
| 1.2 | 1.30 | 2.00 | 2.00 | 1.77 |
| 2.1 | 5.00 | 5.00 | 5.00 | 5.00 |
| 2.2 | 2.45 | 3.00 | 2.55 | 2.67 |
| 3.1 | 0.22 | 0.23 | 0.30 | 0.25 |
| 3.2 | 0.33 | 0.35 | 0.38 | 0.35 |
| 4.1 | 0.30 | 0.41 | 1.05 | 0.59 |
| 4.2 | 0.35 | 0.35 | 1.05 | 0.58 |
| 5.1 | 1.30 | 1.40 | 1.45 | 1.38 |
| 5.2 | 1.45 | 1.50 | 2.15 | 1.70 |
| 6.1 | 1.55 | 2.10 | 2.15 | 1.93 |
| 6.2 | 1.25 | 2.31 | 2.33 | 1.96 |
| 7.1 | 3.50 | 4.20 | 4.30 | 4.00 |
| 7.2 | 3.40 | 4.25 | — | 2.55 |
| 8.1 | 4.20 | 4.49 | — | 2.90 |
| 8.2 | — | — | — | 0.00 |
| 3.2-A | 2.40 | 3.10 | 3.5 | 3.00 |
| 3.2-B | | | | 0.00 |
| 3.2-2 | | | | 0.00 |

Example 4

Foil Dependent Flow

Test strips were produced having a fluid passage consisting of or leading into an area of micropillars having the following dimensions: 69 μm in height. 46 μm in diameter and placed at approximately 29 μm distance or distances from each other. The flow channel had a length of about 25 mm and a width of 4 mm. The distal end—relative to the sample addition—as covered with an adhesive foil. Different foils having hydrophilic and hydrophobic adhesives were tested (samples provided by Adhesives Research Inc. USA).

Flow was tested using phosphate buffered saline with an addition of 0.015% Tween-20. The results are shown in Table 4.

TABLE 4

Effect of foil on flow velocity in a micropillar structure

| Width (*): | 4 mm Flow (μL/min) | 2 mm Flow (μL/min) | Tot. vol. (μl) |
|---|---|---|---|
| None (open structure) | 11 | 7 | 40 |
| Hydrophilic foil | 15 | 8 | 30 |
| Hydrophobic foil | VS | VS | NA |

VS = Very Slow
NA = Not applicable
(*) Width of fluid passage

The results show that covering the distal end of the wider fluid passage (4 mm) with a hydrophilic foil significantly increased the flow velocity. It is likely that the lesser improvement achieved in the more narrow fluid passage (2 mm) is accountable to structural differences. In a narrow fluid passage the effect of the exposed sides becomes greater. It is contemplated that. by adjusting the properties of the adhesive e.g. by choosing different degrees of wetting behaviour or hydrophilicity the flow velocity can be accurately adjusted for various sample fluids.

In general all experimental results show that the inventive concept works in practice. and that the provision of an absorbing zone significantly increased the absorption capacity and flow velocity in a device according to the invention. The experiments using a foil intimately arranged on projections or the micropillar structure show that not only does this define the volume very accurately it also influences the flow velocity.

Although the invention has been described with regard to its preferred embodiments which comprise the best mode presently known to the inventors it should be understood that various changes and modifications as would be obvious to one having the ordinary skill in this art may be made without departing from the scope of the invention as set forth in the claims appended hereto.

The invention claimed is:

1. An assay device comprising a lid and a base, said base comprising a sample addition zone, a reaction zone and an absorbing zone, each of said zones being in fluid connection and component parts of a defined fluid passage leading from the sample addition zone to the absorbing zone, said device further comprising:

a) a sample addition well integrated in the lid;

b) the absorbing zone comprising an area on an non-porous substrate defining said base, said absorbing zone having projections that are perpendicular relative to said substrate, the area of said absorbing zone being directly covered by a foil in which said foil, said projections and said substrate define a volume which together with the volume of the fluid passage further define a sample volume subjected to the assay device and in which said foil or an adhesive attaching said foil to said projections of said absorbing zone has hydrophilic properties that increase the flow velocity of fluid along said fluid passage;

c) each of the zones of said defined fluid passage comprising projections perpendicular relative to said base, said projections commonly having a height, diameter and center to center distance between the projections such that lateral capillary flow of said fluid from said sample addition zone toward said absorbing zone along said defined fluid passage is achieved by said projections; and d) at least one filter disposed between the sample addition well and the sample addition zone, wherein said at least one filter is a hydrophilic polymeric membrane capable of separating red blood cells from plasma, and wherein said at least one filter is in contact with the perpendicular projections in the sample addition zone and in which the flow rate of fluid through said assay device along said defined fluid passage is controlled by selection of the hydrophilic properties of said foil or said adhesive attaching said foil to said projections of said absorbing zone and in which the foil solely covers the absorbing zone of the assay device.

2. The assay device according to claim 1, wherein the fluid passage is an integrated part of the base.

3. The assay device according to claim 1, wherein the assay device further comprises a bottom, said bottom including an opening enabling an assay result to be read from said device.

4. The assay device according to claim 1, wherein the base is transparent, enabling reading of an assay result through said base.

5. The assay device according to claim 1, comprising detection conjugate pre-dispensed in or near the sample addition zone.

6. The assay device according to claim 1, wherein the sample addition well comprises a device preventing a pipette from being inserted through the filter.

7. The assay device according to claim 1, wherein the lid includes a top surface and side walls, said lid having means for fitting to a bottom surface of said base.

* * * * *